Feb. 10, 1959 H. C. SWIM Plant Pat. 1,809
ROSE PLANT
Filed March 17, 1958
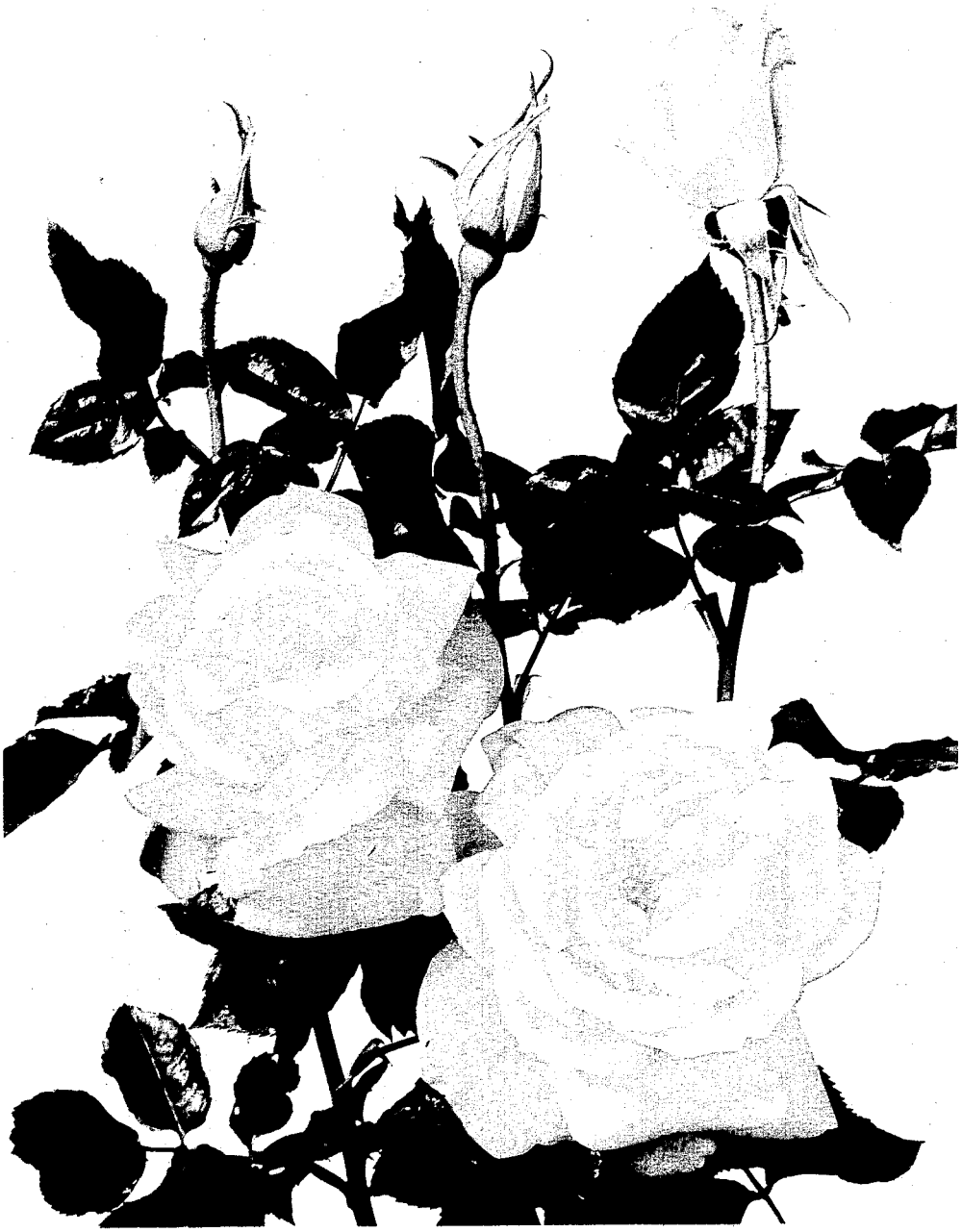
Inventor.
H. C. Swim
By: Robb & Robb
Attorneys.

United States Patent Office

Plant Pat. 1,809
Patented Feb. 10, 1959

1,809

ROSE PLANT

Herbert C. Swim, Ontario, Calif., assignor to Armstrong Nurseries, Inc., Ontario, Calif., a corporation of California Application March 17, 1958, Serial No. 722,109

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Signora" (Plant Patent No. 201).

The primary objective of this breeding was to produce a new rose which combines the most desirable characteristics of the two parent varieties, and at the same time, eliminates some of the disadvantages of the respective parent varieties. This objective was fully achieved, along with other improvements, as evidenced by the following unique combination of features which are outstanding in the new variety:

(1) Very vigorous, upright and relatively floriferous habits of growth;

(2) Large, attractive, glossy dark green foliage;

(3) A habit of bearing flowers singly on long stems;

(4) Long, attractive, urn-shaped buds;

(5) Usually semi-double flowers, but sometimes double; and (6) A general color tonality of the flowers corresponding to Claret Rose, with a variable blend of yellow and pink on the reverse side of the flower petals.

In comparison with its seed parent, "Charlotte Armstrong," the plant of the new variety is quite upright and bears glossy dark green foliage, whereas the plant of this parent is more spreading, and has relatively dull medium green foliage; the flowers of the new variety are usually semi-double, instead of double like those of "Charlotte Armstrong"; and the general Claret Rose flower color, combined with a variable blend of pink and yellow on the reverse side of the petals, is quite different from the flower color of "Charlotte Armstrong," which ranges from blood red to cerise.

As compared with its pollen parent, "Signora," the new variety is generally more vigorous in its habit of growth; the bud is usually longer; the flowers are usually semi-double instead of double like those of "Signora," and have fewer petaloids; and although relatively similar in general color tonality, the flowers of the new variety have a somewhat darker and more red coloring.

Asexual reproduction of the new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Charlotte Armstrong."

*Pollen parent.*—"Signora."

Propagation: Holds its distinguishing characteristics through succeeding propagations by budding.

*Flower*

Locality where grown and observed: Ontario, California.

Flowers borne: Usually singly; on strong, long stems; occasionally, very vigorous branches breaking from heavy canes bear from 3 to 5 long-stemmed flowers in a cluster.

Quantity of bloom: Abundant, outdoors.

Continuity: Nearly continuous during growing season.

Fragrance: Strong. Nature—spicy.

Bud:

*Peduncle.*—From average length to long; heavy caliper; erect; smooth, except for numerous small prickles and stipitate glands of various sizes. Color—near Lime Green, Plate XXXI (Ridgway), overlaid with near Ocher Red, Plate XXVII (Ridgway) on the side exposed to the sun.

*Before calyx breaks.*—Size—from medium to large. Form—from medium length to long; ovoid; usually with slender foliaceous parts extending beyond the tip of the bud equal to ¼ or more of its length.

*As calyx breaks.*—Color—between Jasper Red, Plate 018/1, page 107 (Wilson) and Delft Rose, Plate 020/1, page 108 (Wilson), blending toward base into near Straw Yellow, Plate 604, page 67 (Wilson).

*Sepals.*—Inner surface with fine, woolly tomentum; margins of alternate sepals lined with fine, woolly tomentum, and others lined with stipitate glands and slender foliaceous parts; outer surface moderately smooth, but with some stipitate glands near margins having such glands.

*As first petal opens.*—Size—large. Form—long; urn-shaped. Color: outside—between Claret Rose, Plate 021/1, page 109 (Wilson) and Claret Rose, Plate 021/2, page 109 (Wilson), blending toward base into near Straw Yellow, Plate 604, page 67 (Wilson); inside—between Claret Rose, Plate 021, page 109 (Wilson) and Claret Rose, Plate 021/1, page 109 (Wilson), sometimes fading toward near Jasper Red, Plate 018/3, page 107 (Wilson) at outer margin, and usually overlaid with veins of between Claret Rose, Plate 021, page 109 (Wilson) and Rose Opal, Plate 022, page 110 (Wilson), fading sometimes toward near Claret Rose, Plate 021/2, page 109 (Wilson) at outer margin, with area at base near attachment near Straw Yellow, Plate 604, page 67 (Wilson).

*Opening.*—Opens up well; usually is not retarded from opening by cold, hot, wet or dry weather.

Bloom:

*Size (when fully open).*—Large; from 4 inches to 5 inches.

*Petalage.*—From semi-double to double; from 18 to 28 petals, plus from 2 to 4 petaloids; arranged regularly.

*Form.*—High-centered and somewhat globular at first, but becoming from cupped to high-centered; petals being at first loosely cupped, with tips of most petals slightly reflexed outward, and with lateral margins of inner petals usually reflexed slightly from ⅔ to ¾ of the petal length, while lateral margins of extreme outer petals are usually reflexed the entire petal length, but becoming later at maturity more loosely cupped with tips of most petals reflexed outward slightly, and with lateral margins of petals reflexed usually the entire petal length.

Petals:

*Texture.*—Moderately leathery. Inside—velvety. Outside—satiny.

*Shape.*—Outside—broadly obovate, with apex flat and usually with one or two notches. Intermediate—obovate, with apex from rounded to flat and with one or two notches. Inside—obovate, with irregular margin, and with apex rounded and having one or two notches.

This description of a newly opened flower was made from a rose grown outdoors in the month of November, at Ontario, California:

*Color.*—Outer petal: outside surface—near Delft Rose, Plate 020/3, page 108 (Wilson), blending toward base into near Straw Yellow, Plate 604, page 67 (Wilson); inside surface—near Rose Opal, Plate 022/1, page 110 (Wilson), sometimes fading toward near Jasper Red, Plate 018/3, page 107 (Wilson) at outer margin, usually overlaid with veins of between Claret Rose, Plate 021, page 109 (Wilson) and Rose Opal, Plate 022, page 110 (Wilson), fading sometimes toward near Claret Rose, Plate 021/2, page 109 (Wilson) at outer margin, and with area at base near attachment near Straw Yellow, Plate 604, page 67 (Wilson). Intermediate petal: outside surface—near Delft Rose, Plate 020/3, page 108 (Wilson), blending toward base into near Straw Yellow, Plate 604, page 67 (Wilson); inside surface—between Vermilion, Plate 18/1, page 18 (Wilson) and Delft Rose, Plate 020/1, page 108 (Wilson), sometimes fading toward near Jasper Red, Plate 018/3, page 107 (Wilson) at outer margin, usually overlaid with veins of between Claret Rose, Plate 021, page 109 (Wilson) and Rose Opal, Plate 022, page 110 (Wilson), fading sometimes toward near Claret Rose, Plate 021/2, page 109 (Wilson) at outer margin, and with area at base near attachment near Straw Yellow, Plate 604, page 67 (Wilson). Inner petal: outside surface—near Delft Rose, Plate 020/3, page 108 (Wilson), blending toward base into near Straw Yellow, Plate 604, page 67 (Wilson); inside surface—near Vermilion, Plate 18/1, page 18 (Wilson), sometimes fading toward Jasper Red, Plate 018/3, page 107 (Wilson) at outer margin, overlaid with veins of between Claret Rose, Plate 021, page 109 (Wilson) and Rose Opal, Plate 022, page 110 (Wilson), fading sometimes toward near Claret Rose, Plate 021/2, page 109 (Wilson) toward outer margin, with area at base near attachment near Straw Yellow, Plate 604, page 67 (Wilson).

This description was made from a rose that was open for three days outdoors in the month of November, at Ontario, California:

*Color.*—Outer petal: outside surface—near Rose Opal, Plate 022/3, page 110 (Wilson), blending into near Straw Yellow, Plate 604, page 67 (Wilson) toward base; inside surface—near Rose Opal, Plate 022/2, page 110 (Wilson), fading to between Delft Rose, Plate 020/3, page 108 (Wilson) and Rose Opal, Plate 022/3, page 110 (Wilson) toward outer margin, overlaid with veins of near Rose Opal, Plate 022, page 110 (Wilson), fading to near Rose Opal, Plate 022/2, page 110 (Wilson) toward outer margin, and with area at base near attachment near Straw Yellow, Plate 604, page 67 (Wilson). Inner petal: outside surface—near Rose Opal, Plate 022/2, page 110 (Wilson), blending into near Straw Yellow, Plate 604, page 67 (Wilson) toward base; inside surface—near Claret Rose, Plate 021/1, page 109 (Wilson), fading to between Delft Rose, Plate 020/3, page 108 (Wilson) and Rose Opal, Plate 022/3, page 110 (Wilson) toward outer margin, overlaid with veins of near Rose Opal, Plate 022, page 110 (Wilson), fading to near Rose Opal, Plate 022/2, page 110 (Wilson) toward outer margin, and with area at base near attachment near Straw Yellow, Plate 604, page 67 (Wilson).

*General color effect.*—Newly opened flower—between Claret Rose, Plate 021, page 109 (Wilson) and Claret Rose, Plate 021/2, page 109 (Wilson). 3-days open—between Claret Rose, Plate 021/1, page 109 (Wilson) and Rose Opal, Plate 022/2, page 110 (Wilson), with some shadings of China Rose, Plate 024/2, page 111 (Wilson).

*Flower longevity.*—On bush in garden—2 or 3 days in November. Cut roses grown outdoors and kept at living-room temperatures—2 or 3 days in November.

*Behavior.*—Drop off cleanly; greater than average tendency for petals to shrivel in hot weather.

*Reproductive organs*

Stamens: Average number; arranged regularly about pistils.

Filaments: From medium length to long; from 5 to 15 mm. in length; most with anthers. Color—near Buttercup Yellow, Plate 5, page 5 (Wilson).

Anthers: Medium size; all open approximately at once. Color: upper side—margins near Saffron Yellow, Plate 7, page 7 (Wilson), with remainder near Lemon Yellow, Plate 4/2, page 4 (Wilson); under side—margins near Saffron Yellow, Plate 7, page 7 (Wilson), with remainder near Lemon Yellow, Plate 4/2, page 4 (Wilson).

Pollen: From moderate to abundant. Color—near Buttercup Yellow, Plate 5, page 5 (Wilson).

Pistils: Many; approximately 90 in number.

Styles: Moderately even; average length; from 4 to 10 mm. in length; average caliper; bunched. Color—upper ⅔ of style near Carmine, Plate 21, page 21 (Wilson), with remainder near Uranium Green, Plate 63/2, page 63 (Wilson).

Stigma: Color—near Nasturtium Orange, Plate 610/2, page 145 (Wilson).

Ovaries: Usually all enclosed in calyx, but some protruding from calyx.

Hips: Average length; globular; smooth; with walls thick and fleshy. Color (⅔ mature)—near Cosse Green, Plate V (Ridgway), shading into near Oil Yellow, Plate V (Ridgway) on side exposed to the sun.

Sepals: Permanent; medium length; curled recurved. Color: inside—near Light Grape Green, Plate XLI (Ridgway); outside—near Biscay Green, Plate XVII (Ridgway).

Seeds: Average number; from 6 to 10 in number per open-pollinated hip; from small to medium size.

*Plant*

Foliage:

*Leaves.*—Compound of usually 3 to 7 leaflets; moderately abundant; large; leathery; glossy.

*Leaflets.*—Shape—from oval to oblong, with apex acute; round base; with margin doubly serrate.

*Color.*—Mature: upper surface—near Dark Dull Yellow-Green, Plate XXXII (Ridgway); under surface—near Light Grape Green, Plate XLI (Ridgway). Young: upper surface—near Deep Olive, Plate XL (Ridgway), variably shaded with near Mineral Red, Plate XXVII (Ridgway); under surface—near Light Grape Green, Plate XLI (Ridgway), heavily shaded with near Deep Corinthian Red, Plate XXVII (Ridgway).

*Rachis (the supporting stem of the compound leaf).*—Average size. Upper side—grooved; with few stipitate glands on edges. Under side—relatively smooth; with stipitate glands and one or two prickles.

*Stipules.*—Medium length; medium width; with points of medium length turned out at an angle of less than 45° and recurved toward the stem.

*Disease resistance.*—Better than average resistance to mildew, as compared with other varieties grown under comparable cultural conditions at Ontario, California.

Growth:

*Habit.*—Bushy; upright; moderately branched.

*Growth.*—Very vigorous.

*Canes.*—From medium caliper to heavy.

*Main stems.*—Color—near Lettuce Green, Plate V (Ridgway), overlaid with near Buffy Olive, Plate XXX (Ridgway) on side exposed to the sun. Large prickles—few; medium length; hooked downward; with narrow base of medium length; color—near Pecan Brown, Plate XXVIII (Ridgway). Small prickles—very few; color—near Pecan Brown, Plate XXVIII (Ridgway). Hairs—none.

*Branches.*—Color—near Parrot Green, Plate VI (Ridgway). Large prickles—from none to few; medium length; hooked downward; with narrow base of medium length; color—near Cinnamon, Plate XXIX (Ridgway). Small prickles—from none to very few; color—near Cinnamon, Plate XXIX (Ridgway). Hairs—none.

*New shoots.*—Color—near Calliste Green, Plate VI (Ridgway), overlaid with near Ocher Red, Plate XXVII (Ridgway) on side exposed to the sun. Large prickles—few; medium length; hooked slightly downward; with narrow base of medium length; color—near Ocher Red, Plate XXVII (Ridgway). Small prickles—from none to few; color—near Ocher Red, Plate XXVII (Ridgway). Hairs—none.

I claim:

A new and distinct variety of rose plant of the hybrid tea class, substantially as herein shown and described, characterized particularly as to novelty by the unique combination of very vigorous, upright and relatively floriferous habits of growth, large, attractive, glossy dark green foliage, a habit of usually bearing flowers singly on long stems, long, attractive urn-shaped buds, usually semi-double but sometimes double flowers, and a general color tonality of the flowers corresponding to near Claret Rose, with a variable blend of yellow and pink on the reverse side of the flower petals.

No references cited.